United States Patent [19]

Aquila et al.

[11] Patent Number: 5,196,609
[45] Date of Patent: Mar. 23, 1993

[54] PREPARATION OF 3-ALKOXYCARBONYL PROPENALS AND 3-DIALKOXYMETHYL PROPENALS

[75] Inventors: Werner Aquila, Mannheim; Hans-Ulrich Scholz, Weisenheim; Hartwig Fuchs, Ludwigshafen; Wolfgang Krause, Mannheim; Joachim Paust; Werner Hoffmann, both of Neuhofen, all of Fed. Rep. of Germany

[73] Assignee: BASF Aktiengesellschaft, Ludwigshafen, Fed. Rep. of Germany

[21] Appl. No.: 844,317

[22] Filed: Mar. 2, 1992

[30] Foreign Application Priority Data

Mar. 5, 1991 [DE] Fed. Rep. of Germany ....... 4106907

[51] Int. Cl.$^5$ ..................... C07C 45/37; C07C 47/277
[52] U.S. Cl. .................................. 568/473; 568/470; 568/471; 568/485; 568/489; 568/496
[58] Field of Search ................ 549/357; 568/449, 470, 568/471, 473, 485, 489, 496

[56] References Cited

U.S. PATENT DOCUMENTS 3,118,930 1/1969 Sisido et al. ........................ 568/491

FOREIGN PATENT DOCUMENTS 2225612 1/1976 Fed. Rep. of Germany ...... 568/471

OTHER PUBLICATIONS

Can. J. Chem. 57, 3354 (1979).

Ars Pharm. 29, (2) 117-22 (1988).

*Primary Examiner*—Werren B. Lone
*Attorney, Agent, or Firm*—Herbert B. Keil

[57] ABSTRACT

The preparation of 3-alkoxycarbonyl propenals and 3-dialkoxymethyl propenals of the general formulae Ia and Ib respectively:

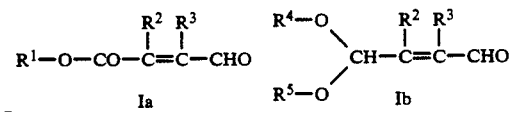

($R^1$=$C_1$-$C_3$-alkyl group; $R^2$ and $R^3$ = hydrogen, methyl, or ethyl; and $R^4$ and $R^5$=$C_1$-$C_4$-alkyl groups, which may be joined to form a 5-membered or 6-membered ring), is effected by reacting a corresponding alcohol of the general formula IIa or IIb

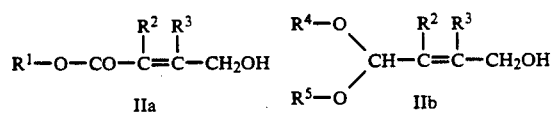

with oxygen or an oxygen-containing gas in the gas phase in the presence of a metal from Group IB of the Periodic Table or a compound of one such metal acting as catalyst.

The target products serve as intermediates for the synthesis of carotenoids.

4 Claims, No Drawings

PREPARATION OF 3-ALKOXYCARBONYL PROPENALS AND 3-DIALKOXYMETHYL PROPENALS

The present invention relates to a novel process for the preparation of 3-alkoxycarbonyl propenals and 3-dialkoxymethyl propenals of the general formulae Ia and Ib below:

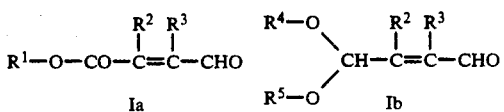

in which $R^1$ denotes a $C_1$–$C_3$-alkyl groups, $R^2$ and $R^3$ denote hydrogen, methyl, or ethyl, and $R^4$ and $R^5$ denote $C_1$–$C_4$-alkyl groups, which may be joined to form a 5-membered ring.

The compounds Ia and Ib are known and serve as intermediates for the synthesis of carotenoids.

U.S. Pat. No. 3,118,930 describes the preparation of 3-alkoxycarbonyl propenals Ia in which $R^2$ denotes hydrogen and $R^3$ denotes a methyl group by reaction of an alkyl 2-methyl-3-bromopropene-1-carboxylate with pyridine to form the pyridinium salt and treatment of the latter with an alcoholic solution of p-nitrosodialkylaniline in the presence of an alkali metal hydroxide, followed by hydrolysis with an acid.

Ars. Phar. 29 (2), 117 (1988) discloses the reaction of methyl 2-methyl-3-bromopropene-1-carboxylate with dimethyl sulfoxide and sodium bicarbonate to form the corresponding 3-methoxycarbonyl propenal Ia.

Can. J. Chem. 57, 3354 (1979) describes the reaction of an alcohol IIa in which $R^1$ is ethyl, $R^2$ is methyl and $R^3$ is hydrogen with manganese dioxide to form the corresponding 3-ethoxycarbonyl propenal Ia.

DE-A 2,225,612 describes the preparation of 3-dialkoxymethyl propenals Ib in which one of the radicals $R^2$ and $R^3$ is hydrogen and the other is methyl by liquid-phase oxidation of the corresponding alcohols IIb with pyridine/sulfur trioxide complexes, pyridine/chromium trioxide complexes, manganese dioxide, or nickel peroxide, and with a chromic acid solution in acetone which has been acidified with sulfuric acid.

In another synthesis route some of said compounds IIb, in which $R^2$ denotes hydrogen only, are formed by aldol condensation of a glyoxal monoacetal with an aldehyde (DE-A 3,617,409).

Furthermore, DE-A 3,603,662 discloses the gas-phase dehydrogenation, catalyzed with a metal from Group IB of the Periodic Table, of a saturated mono-acetalized alcohol using oxygen or an oxygen-containing gas to form a saturated mono-acetalized aldehyde.

However, such prior art processes are unsatisfactory due to the high engineering input involved and to the fact that expensive oxidizing agents are necessary.

It is thus an object of the invention to provide 3-alkoxycarbonyl propenals Ia and 3-dialkoxymethyl propenals Ib in a simpler and more economical manner.

Accordingly, we have found a novel process for the preparation of a 3-alkoxycarbonyl propenal or a 3-dialkoxymethyl propenal of the general formula Ia and Ib respectively:

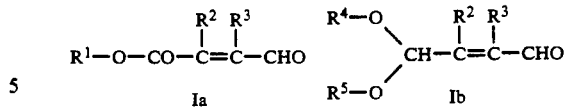

in which $R^1$ denotes a $C_1$–$C_3$-alky group, $R^2$ and $R^3$ denote hydrogen, methyl, or ethyl, and $R^4$ and $R^5$ denote $C_1$–$C_4$-alkyl groups, which may be joined to form a 5-membered or 6-membered ring, wherein a corresponding alcohol of the general formula IIa and IIb

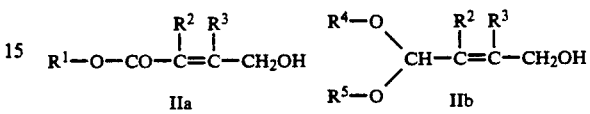

is reacted with oxygen or an oxygen-containing gas in the gas phase in the presence of a metal from Group IB of the Periodic Table or a compound of one such metal acting as catalyst.

The starting materials II are known or can be prepared by known methods. For example, the compounds IIa are formed by reacting ethyl 1-methyl-prop-2-ene carboxylate with m-chloroperbenzoic acid to produce the corresponding epoxide, followed by treatment of the latter with potassium carbonate in ethanol [Can. J. Chem. 57, 3354 (1979)]. The starting materials IIb may be prepared, for example, by acetalizing 4-acetoxybut-2-en-1-als with alcohols and converting the products to the free alcohols by removing the acetyl groups [Liebigs Ann. Chem., 2194 (1976)].

With a view to the target products I, those compounds II are particularly preferred in which one of the radicals $R^2$ and $R^3$ is hydrogen and the other methyl.

For technological reasons, the most important compounds II are those in which $R^4$ and $R^5$ together form a neopentylene radical. Other preferred meanings of $R^4$ and $R^5$ are radicals derived from 1,2-ethylene glycol or 1,3-propylene glycol and open-chain radicals such as, in particular, methyl.

The catalysts to be used in the process of the invention are metals from Group IB of the Periodic Table or compounds of such metals.

The catalysts may be used in metallic form or in the form of salts or oxides.

Suitable catalysts in metallic form are, preferably, copper and, more preferably, silver. The metals are preferably used in the form of supported catalysts, and preferred supports are ceramics, such as porcelain, and magnesium oxide, aluminum oxide, silicon oxide, silicon carbide, titanium oxide, zinc oxide, lanthanum oxide, aluminum silicate, or mixtures of these materials and, most preferably, steatite. A particularly preferred combination is silver on steatite.

The supported catalysts preferably have a content of active Group IB metal of from 0.01% to 50% w/w, preferably from 0.05% to 30% w/w, and more preferably from 1% to 20% w/w, based on the total weight of support and active metal, calculated as metal.

The catalysts may take the form, as required, of extrudates having a length of from 2 to 4 mm, pellets having a diameter of from 3 to 5 mm, gravel having a maximum particle size ranging from 0.05 to 1 mm, preferably 0.1 to 0.5 mm, or powder having particle sizes ranging from 0.05 to 0.5 mm. The powder may be used in a fluidized bed if desired. Bowl-shaped catalysts having a spherical curvature of from 1 to 10 mm in diameter and containing steatite as supporting material are particularly preferred.

The throughput of compound II through the catalyst during continuous operation is generally between 0.2 and 2 tons and preferably between 0.3 and 1.5 tons per $m^2$ of catalyst cross-section per hour.

Oxidation of the starting materials II to the target products I is carried out using oxygen or an oxygen-containing gas, a particularly preferred oxidizing agent being air.

The molar ratio of oxygen to starting material II is advantageously from 0.1:1 to 4:1 and preferably from 0.2:1 to 2:1.

The reaction is usually carried out at a temperature of from 300° to 700° C. and preferably from 320° to 500° C.

In general, the reaction is carried out at a pressure of from 0.0005 to 2 bar and in particular from 0.001 to 1 bar. The residence time of the gas mixture in the reaction chamber is normally from 0.0005 to 1 second and usually from 0.001 to 0.5 second.

We recommend that the oxygen be used not in pure form but in admixture with an inert gas in a ratio of inert gas to oxygen of from 1:1 to 50:1 and in particular from 3:1 to 20:1, by volume. Preferred inert gases are carbon monoxide, carbon dioxide, noble gases, and especially nitrogen. The use of air as oxidizing gas is particularly preferred.

To facilitate volatilization of the starting materials II, it is recommended that they be used in the form of solutions, which are then evaporated in their entirety. Preferred solvents are water and, in particular, organic solvents. Particularly suitable organic solvents are ketones such as acetone and methylethyl ketone, ethers such as tetrahydrofuran, dioxane, and diisopropyl ethyl, esters such as ethyl acetate, and hydrocarbons such as toluene. It is usual to use the solvent and starting material II in a ratio of from 0.05:1 to 5:1 and preferably from 0.1:1 to 3:1. Evaporation may be facilitated by the co-use of a carrier gas such as one of the aforementioned inert gases, especially nitrogen.

The oxidation takes place in the gas phase, both a fixed bed reaction and a gas-phase reaction in a fluidized bed being possible. A highly economical embodiment of the process of the invention consists in execution thereof over a fixed-bed catalyst. This is carried out by evaporating the alcohol II optionally together with a solvent and/or carrier gas and passing the resulting gaseous phase, preferably in admixture with an inert gas, over a solid catalyst together with oxygen or an oxygen-containing gas.

The reaction mixture is worked up to provide the target product I in conventional manner, usually by cooling the reaction gases and causing them to be absorbed in an inert solvent. The desired product can then be purified by fractional distillation. Preferred examples of suitable inert solvents are hexane, toluene, methyl-t-butyl ether, and, in particular, water. A particularly suitable solvent is the target product itself.

It is advisable, particularly with a view to reducing acid-catalyzed formation of bis-acetal, to stabilize the effluent products with an alkali metal hydroxide, alkaline earth metal hydroxide, alkali metal carbonate or bicarbonate, or alkaline earth metal carbonate or bicarbonate. Particularly good results are achieved using an aqueous urotropine solution in an amount governed by the acid number of the effluent product.

The 3-alkoxycarbonyl propenals Ia and 3-dialkoxymethyl propenals Ib produced in a simple and economical manner by the process of the invention serve as intermediates for the synthesis of carotenoids. For example, the reaction of 3-methylfumardialdehyde mono-1-acetals Ib with the ylide of β-ionylidene-ethyltriphenyl-phosphonium salts with subsequent hydrolysis in the presence of an aqueous acid yields retinal (vitamine $A_1$ aldehyde). The use of the corresponding compound Ia yields retinic acid. Retinal can be converted to β-carotene by simple Wittig olefination with the retinyl-triphenyl-phosphonium salt followed by hydrolysis. The reaction of a retinyltriphenyl-phosphonium salt with a 2-methylfumardialdehyde mono-1-acetal Ib in a Wittig reaction followed by hydrolysis gives β-apo-$C_{25}$-carotenal.

EXAMPLES

1. Preparation of 2-methylbut-2-ene-1,4-dial-1-neopentylglycol-acetal 50 g of 4-hydroxy-2-methylbut-2-ene-1-neopentyl-glycol-acetal were evaporated with 12.8 l of hot air over a period of 1 hour under a pressure of 80 mbar and at a temperature of 435° C. and then passed over 12 g of solid silver catalyst (4% w/w of silver on steatite) for a time of 0.2 second.

Conventional working-up procedures involving the absorption of the effluent with a 10% urotropine solution gave the 2-methylbut-2-ene-1,4-dial-1-neopentyl-glycol-acetal in a yield of 63% and a selectivity of 90%.

2. Preparation of 3-methylbut-2-ene-1,4-dial-1-neopentylglycol-acetal 50 g of 4-hydroxy-3-methylbut-2-ene-1-neopentyl-glycol-acetal and 10.4 l of air were passed, per hour, over the silver catalyst as described in Example 1 at a pressure of 80 mbar and a temperature of 430° C. The crude effluent was then treated with a 10% urotropine solution.

The 3-methylbut-2-ene-1,4-dial-1-neopentylglycol-acetal was obtained in a yield of 83% and a selectivity of 93%.

3. Preparation of ethyl 2-methyl-4-oxo-2-butenate 50 g of ethyl 4-hydroxy-2-methyl-2-butenate and 12.8 l of air were passed, per hour, over the silver catalyst as described in Example 1 at a pressure of 500 mbar and a temperature of 400° C. The crude effluent was then subjected to fractional distillation.

The ethyl 2-methyl-4-oxo-2-butenate was obtained in a yield of 68% and a selectivity of 75%.

We claim:

1. A process for the preparation of a 3-alkoxycarbonyl propenal or 3-dialkoxymethyl propenal of the formulae Ia and Ib respectively

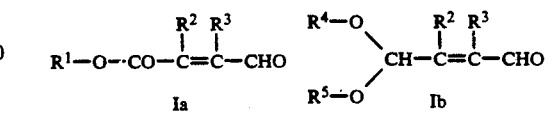

in which $R^1$ denotes a $C_1$-$C_3$-alkyl group, $R^2$ and $R^3$ denote hydrogen, methyl, or ethyl, and $R^4$ and $R^5$ denote $C_1$-$C_4$-alkyl groups, which may be joined to form a 5-membered or 6-membered ring, wherein a corresponding alcohol of the formula IIa or IIb

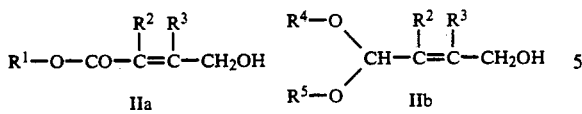   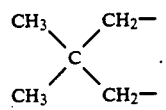

is reacted with oxygen or an oxygen-containing gas in the gas phase in the presence of a metal from Group IB of the Periodic Table or a compound of one such metal acting as catalyst at 300° to 700° C. and 0.0005 to 2 bar.

2. A process as claimed in claim 1, wherein $R^4$ and $R^5$ together stand for a neopentylene radical:

$$CH_3 \diagdown \diagup CH_2- \\ C \\ CH_3 \diagup \diagdown CH_2-$$

3. A process as claimed in claim 1, wherein the catalyst used for the reaction is a silver catalyst.

4. A process as claimed in claim 2, wherein the catalyst used for the reaction is a silver catalyst.

* * * * *